United States Patent
Watson et al.

(10) Patent No.: US 8,346,333 B2
(45) Date of Patent: Jan. 1, 2013

(54) SYSTEMS AND METHODS FOR ESTIMATING VALUES OF A CONTINUOUS WAVELET TRANSFORM

(75) Inventors: James Nicholas Watson, Dunfermline (GB); Paul Stanley Addison, Edinburgh (GB); Braddon M. Van Slyke, Arvada, CO (US)

(73) Assignee: Nellcor Puritan Bennett Ireland, Mervue Galway ( * ) Notice: Subject to any disclaimer, the term of this patent is extended or adjusted under 35 U.S.C. 154(b) by 824 days.

(21) Appl. No.: 12/512,132

(22) Filed: Jul. 30, 2009

(65) Prior Publication Data

US 2011/0028813 A1  Feb. 3, 2011

(51) Int. Cl.
- A61B 5/1455 (2006.01)
- A61B 5/00 (2006.01)
- G01N 33/48 (2006.01)

(52) U.S. Cl. .......... 600/336; 702/19; 600/502; 600/529
(58) Field of Classification Search .................. 600/310, 600/322, 323, 324, 330, 336, 502, 529; 356/41; 702/19, 189, 190; 700/1; 365/94
See application file for complete search history.

(56) References Cited

U.S. PATENT DOCUMENTS

| | | |
|---|---|---|
| 4,289,141 A | 9/1981 | Cormier |
| 5,439,483 A | 8/1995 | Duong-Van |
| 5,590,650 A | 1/1997 | Genova |
| 5,632,272 A | 5/1997 | Diab et al. |
| 5,778,881 A | 7/1998 | Sun et al. |
| 5,795,304 A | 8/1998 | Sun et al. |
| 5,797,840 A | 8/1998 | Akselrod |
| 5,827,195 A | 10/1998 | Lander |
| 5,967,995 A | 10/1999 | Shusterman et al. |
| 6,002,952 A | 12/1999 | Diab et al. |
| 6,036,653 A | 3/2000 | Baba et al. |
| 6,094,592 A | 7/2000 | Yorkey |
| 6,095,984 A | 8/2000 | Amano et al. |
| 6,117,075 A | 9/2000 | Barnea |
| 6,129,675 A | 10/2000 | Jay |

(Continued)

FOREIGN PATENT DOCUMENTS

JP  09-084776  3/1997

(Continued)

OTHER PUBLICATIONS

Addison, Paul S., The Illustrated Wavelet Transform Handbook, Taylor & Francis Group, 2002.

(Continued)

*Primary Examiner* — Eric Winakur

(57) ABSTRACT

According to embodiments, techniques for estimating scalogram energy values in a wedge region of a scalogram are disclosed. A pulse oximetry system including a sensor or probe may be used to receive a photoplethysmograph (PPG) signal from a patient or subject. A scalogram, corresponding to the obtained PPG signal, may be determined. In an arrangement, energy values in the wedge region of the scalogram may be estimated by calculating a set of estimation locations in the wedge region and estimating scalogram energy values at each location. In an arrangement, scalogram energy values may be estimated based on an estimation scheme and by combining scalogram values in a vicinity region. In an arrangement, the vicinity region may include energy values in a resolved region of the scalogram and previously estimated energy values in the wedge region of the scalogram. In an arrangement, one or more signal parameters may be determined based on the resolved and estimated values of the scalogram.

20 Claims, 15 Drawing Sheets

U.S. PATENT DOCUMENTS

| | | |
|---|---|---|
| 6,135,966 A | 10/2000 | Ko |
| 6,171,257 B1 | 1/2001 | Weil et al. |
| 6,171,258 B1 | 1/2001 | Karakasoglu et al. |
| 6,208,951 B1 | 3/2001 | Kumar et al. |
| 6,293,915 B1 | 9/2001 | Amano et al. |
| 6,325,761 B1 | 12/2001 | Jay |
| 6,361,501 B1 | 3/2002 | Amano et al. |
| 6,393,311 B1 | 5/2002 | Edgar, Jr. et al. |
| 6,430,525 B1 | 8/2002 | Weber et al. |
| 6,561,986 B2 | 5/2003 | Baura |
| 6,608,934 B2 | 8/2003 | Scheirer |
| 6,654,623 B1 | 11/2003 | Kastle |
| 6,810,277 B2 | 10/2004 | Edgar, Jr. et al. |
| 6,931,269 B2 | 8/2005 | Terry |
| 6,993,377 B2 | 1/2006 | Flick et al. |
| 6,999,904 B2 | 2/2006 | Weber et al. |
| 7,001,337 B2 | 2/2006 | Dekker |
| 7,020,507 B2 | 3/2006 | Scharf et al. |
| 7,035,679 B2 | 4/2006 | Addison |
| 7,043,293 B1 | 5/2006 | Baura |
| 7,054,453 B2 | 5/2006 | Causevic |
| 7,054,454 B2 | 5/2006 | Causevic et al. |
| 7,079,888 B2 | 7/2006 | Oung |
| 7,085,436 B2 * | 8/2006 | Akhan et al. .................. 382/298 |
| 7,171,269 B1 | 1/2007 | Addison |
| 7,173,525 B2 | 2/2007 | Albert |
| 7,203,267 B2 | 4/2007 | De Man et al. |
| 7,225,013 B2 | 5/2007 | Geva et al. |
| 7,254,500 B2 | 8/2007 | Makeig |
| 7,289,835 B2 | 10/2007 | Mansfield |
| 7,477,571 B2 | 1/2009 | Melese et al. |
| 7,499,835 B2 | 3/2009 | Weber et al. |
| 7,515,949 B2 | 4/2009 | Norris |
| 7,519,488 B2 | 4/2009 | Fu |
| 7,523,011 B2 | 4/2009 | Akiyama et al. |
| 7,566,306 B2 | 7/2009 | Fujiwara et al. |
| 7,869,994 B2 * | 1/2011 | Nongpiur et al. ............. 704/226 |
| 2005/0043616 A1 | 2/2005 | Chinchoy |
| 2006/0211930 A1 | 9/2006 | Scharf et al. |
| 2006/0258921 A1 | 11/2006 | Addison et al. |
| 2006/0265022 A1 | 11/2006 | John et al. |
| 2007/0021673 A1 | 1/2007 | Arbel et al. |
| 2007/0073120 A1 | 3/2007 | Li et al. |
| 2007/0073124 A1 | 3/2007 | Li et al. |
| 2007/0167694 A1 | 7/2007 | Causevic et al. |
| 2007/0167851 A1 | 7/2007 | Vitali et al. |
| 2007/0282212 A1 | 12/2007 | Sierra et al. |
| 2008/0045832 A1 | 2/2008 | McGrath |
| 2008/0082018 A1 | 4/2008 | Sackner et al. |
| 2008/0214903 A1 | 9/2008 | Orbach |
| 2008/0243021 A1 | 10/2008 | Causevic et al. |

FOREIGN PATENT DOCUMENTS

| | | |
|---|---|---|
| WO | WO 01/25802 | 4/2001 |
| WO | WO 01/62152 | 8/2001 |
| WO | WO 03/055395 | 7/2003 |
| WO | WO 2004/105601 | 12/2004 |
| WO | WO 2005/096170 | 10/2005 |
| WO | WO 2006/085120 | 8/2006 |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Leonard, Paul A., Douglas, J. Graham, Grubb, Nel R., Clifton, David, Addison, Paul S., Watson, James N., "A Fully Automated Algorithm for the Determination of Respiratory Rate from the Photoplethysmogram," Journal of Clinical Monitoring and Computing, 2006.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

* cited by examiner

SYSTEMS AND METHODS FOR ESTIMATING VALUES OF A CONTINUOUS WAVELET TRANSFORM

SUMMARY

The present disclosure is related to signal processing systems and methods, and more particularly, to systems and methods for estimating scalogram energy values in a wedge region of a scalogram.

In an embodiment, a photoplethysmograph (PPG) signal may be received from a pulse oximetry system, including from a sensor coupled to the pulse oximetry system. Processing equipment may be used to transform the PPG signal. In an arrangement, the processing equipment may transform the PPG signal using a continuous wavelet transform, and a scalogram may be generated from the transformed PPG signal. In an arrangement, one or more energy values in a wedge region of the scalogram may be estimated using an estimated scheme. Further, one or more signal parameters related to the PPG signal may be determined or identified based on the estimated energy values. In an arrangement, the determined signal parameters may be output to an output device, including, for example, a display or monitor device. In an arrangement, the output device may include an audible alarm.

In an embodiment, the estimation of energy values in the wedge region of the scalogram may rely on determining a set of estimation points and a set of locations corresponding to the estimation points in the wedge region of the scalogram. In an arrangement, the estimation points may be placed in a grid-like structure in the wedge region. In an arrangement, a set of estimation parameters may be determined. The set of estimation parameters may include, for example, a statistical estimation technique, a probability of an event, and/or a specification of a size and shape of a vicinity region. In an arrangement, the vicinity region may enclose a point to be estimated within the wedge region of the scalogram, and the estimation process may rely on previously estimated values and resolved scalogram values within the vicinity region to estimate the current point. In an arrangement, the vicinity region may not enclose the point that is to be estimated within the wedge region of the scalogram.

In an embodiment, the determined signal parameters may include a patient respiration rate, a patient oxygen saturation level, a patient respiration effort level, and/or any suitable combination thereof. In an arrangement, one or more confidence metrics may be determined, where the confidence metrics relate to the determined signal parameters. For example, in an arrangement, each of the confidence metrics may provide statistical or probability-based information on a signal parameter, that includes information on the reliability of the signal parameter. In an arrangement, the confidence metrics may be compared to a constraint set, and the estimation scheme may be rerun with different parameters if the confidence metrics do not jointly satisfy the constraint set. In an arrangement, the determination of the confidence metrics may depend on determining energy values and energy structures in a pulse band and/or noise band of the scalogram.

In an arrangement, the size and shape of the vicinity region may be determined based on one or more characteristics of the signal parameters that are to be determined. For example, the size and shape of the vicinity region may be determined based on expected or previously observed patterns that one or more of the parameters may create in the scalogram.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
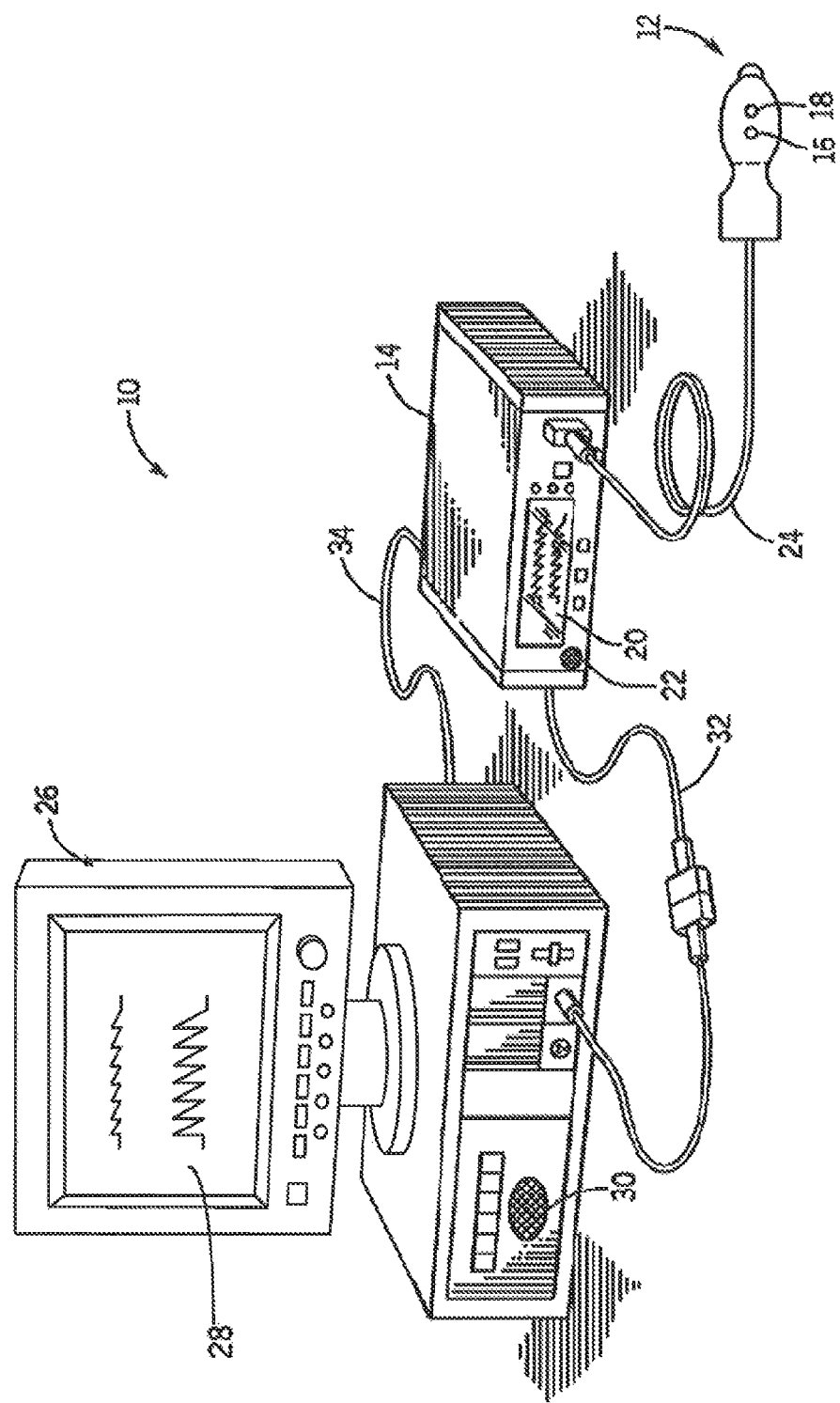
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t) = I_o(\lambda)\exp(-(s\beta_o(\lambda) + (1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_0 + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_T(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t) = [I(t_2, \lambda_{IR}) - I(t_1, \lambda_{IR})]I(t_1, \lambda_R)$$

$$y(t) = [I(t_2, \lambda_R) - I(t_1, \lambda_R)]I(t_1, \lambda_{IR})$$

$$y(t) = Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "$SpO_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
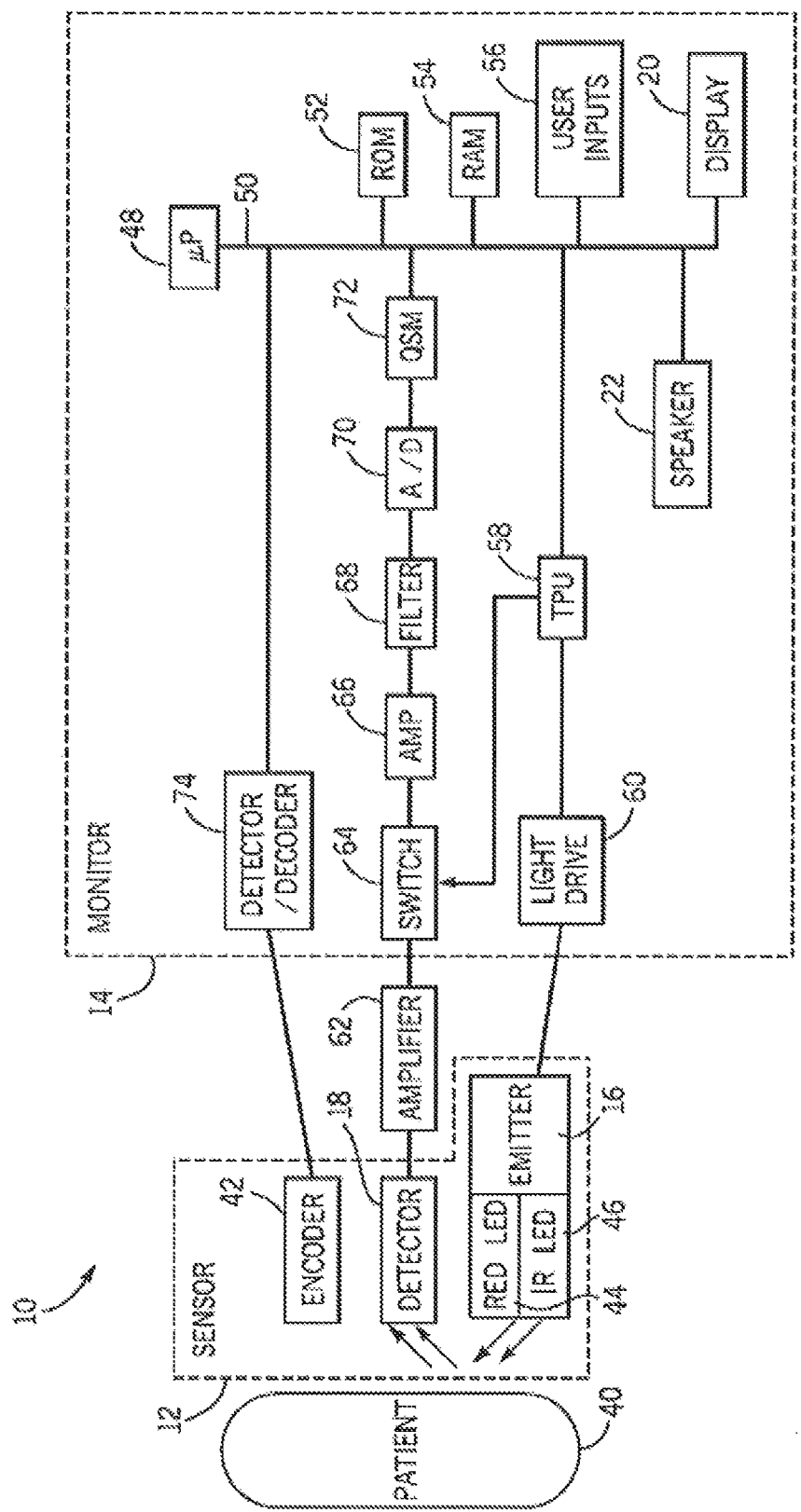
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patients tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SPO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals. PPG signals may be taken herein to mean processed or filtered PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \qquad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \qquad (10)$$

where '||' is the modulus operator. The scalogram may be rescaled for useful purposes. One common rescaling is defined as $$S_R(a, b) = \frac{|T(a, b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \qquad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figures 3A, 3B:
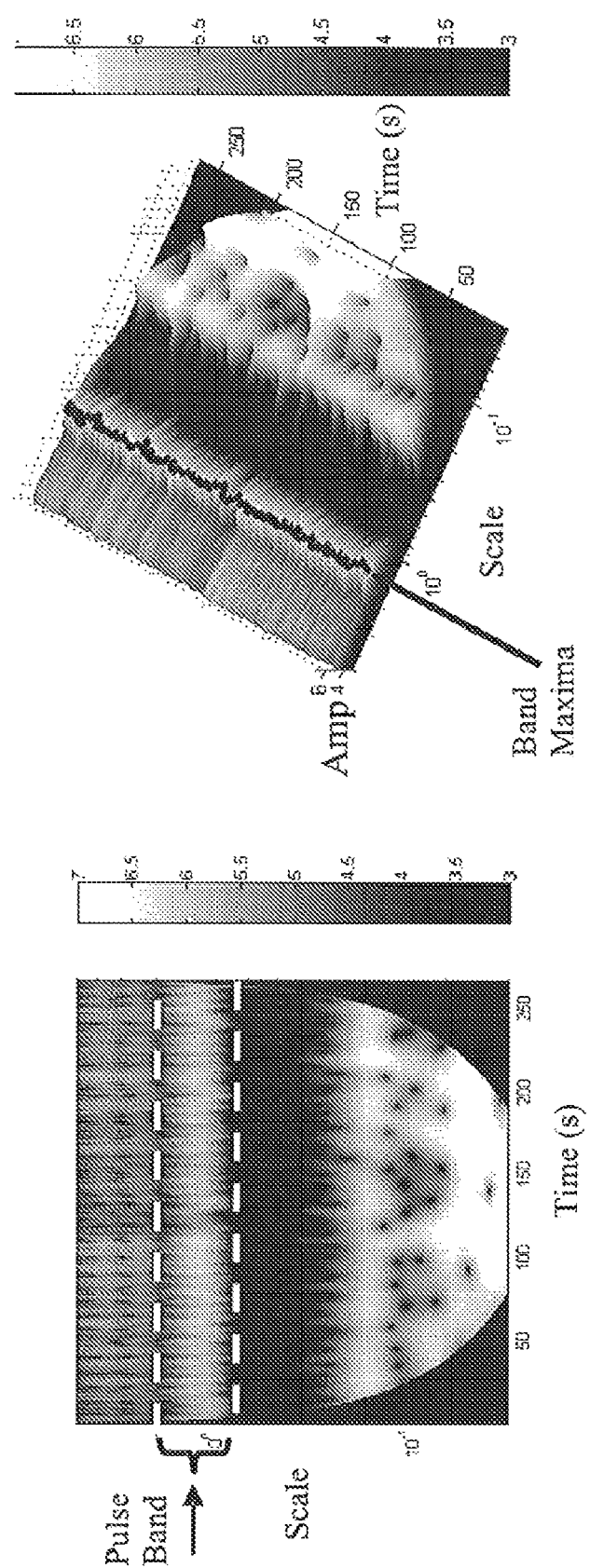
FIGS. 3(a) and 3(b) show illustrative views of a scalogram derived from a PPG signal in accordance with an embodiment.

Pertinent repeating features in a signal give rise to a time-scale band in wavelet space or a resealed wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable resealing of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
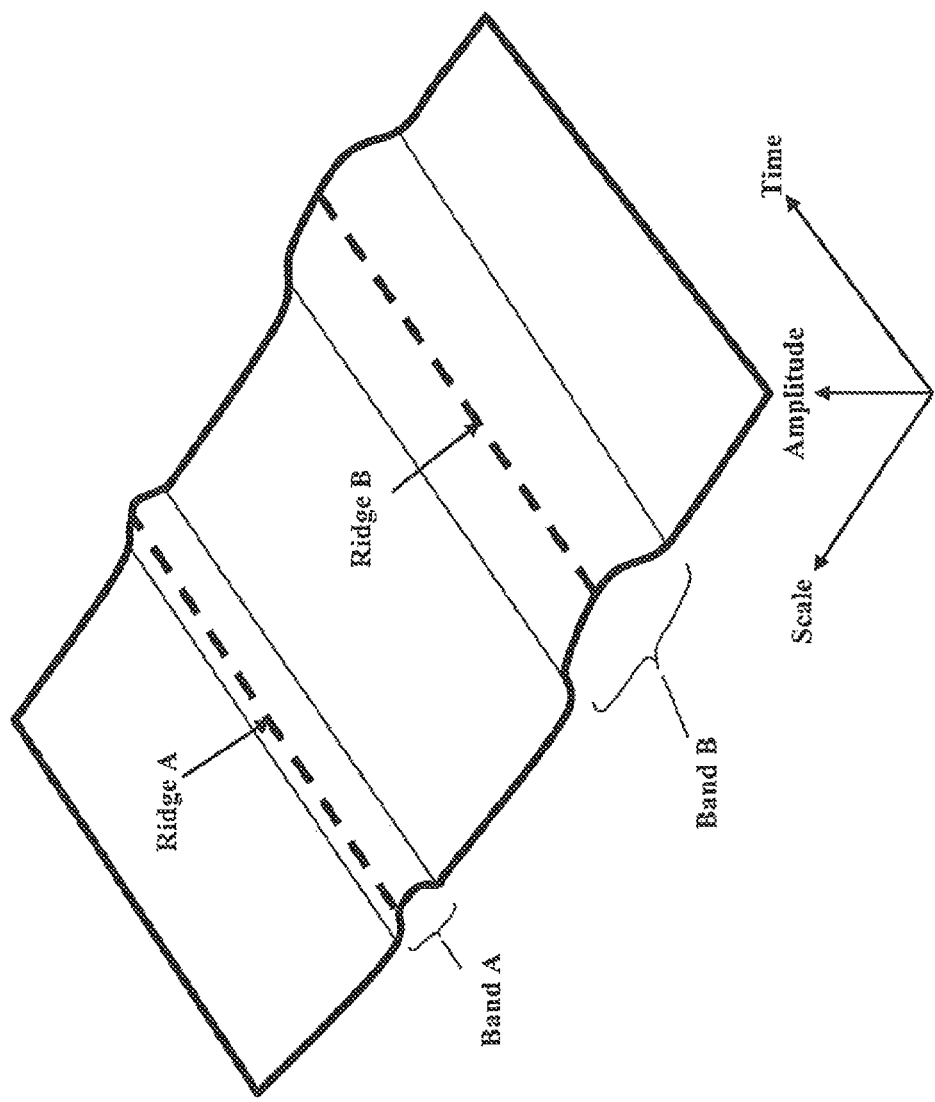
FIG. 3(c) shows an illustrative scalogram derived from a signal containing two pertinent components in accordance with an embodiment.
Figure 3D:
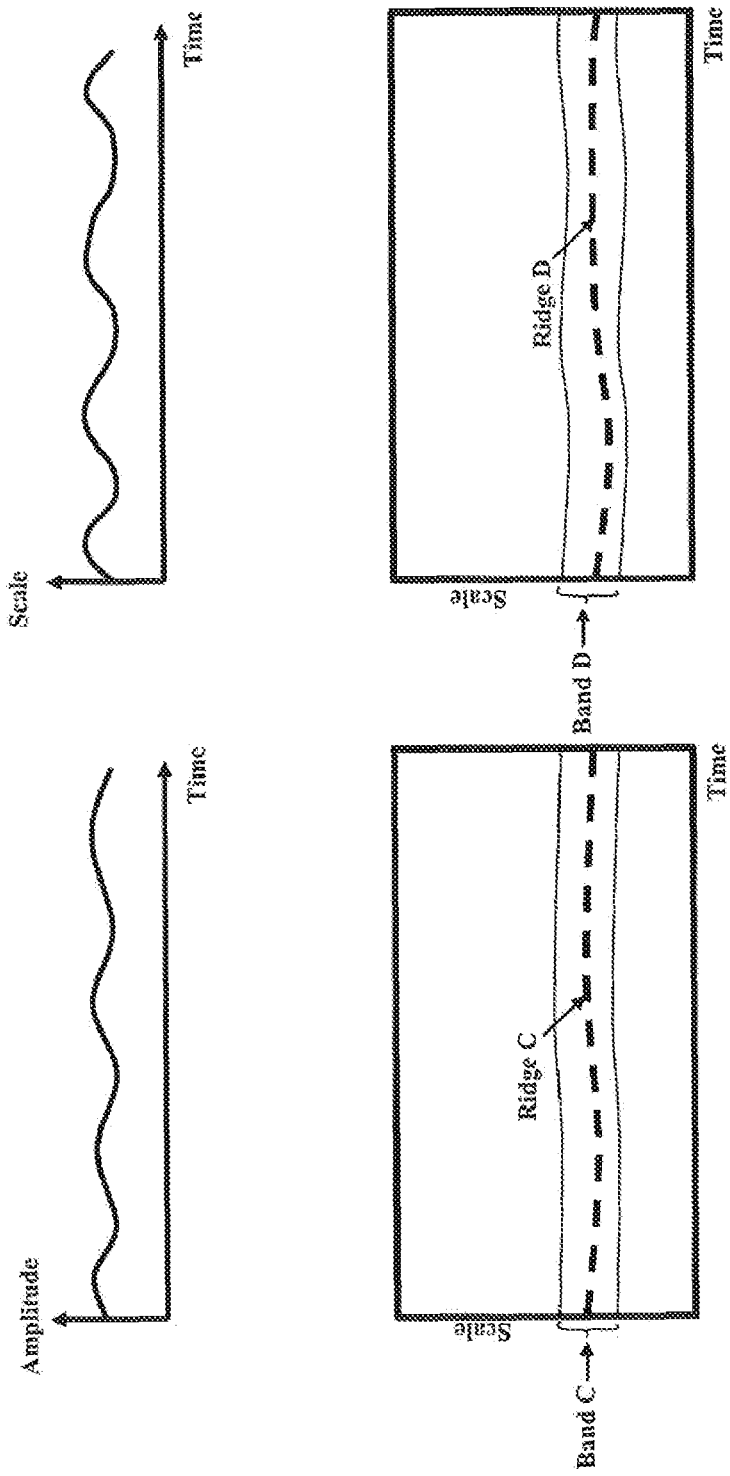
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_0^{\infty} T(a,b) \psi_{a,b}(t) \frac{da\,db}{a^2} \quad (16)$$

where $C_g$ is a scalar value known as the admissibility constant. It is wavelet type dependent and may be calculated from:

$$C_g = \int_0^\infty \frac{|\hat{\psi}(f)|^2}{f} df \quad (17)$$

Figure 3E:
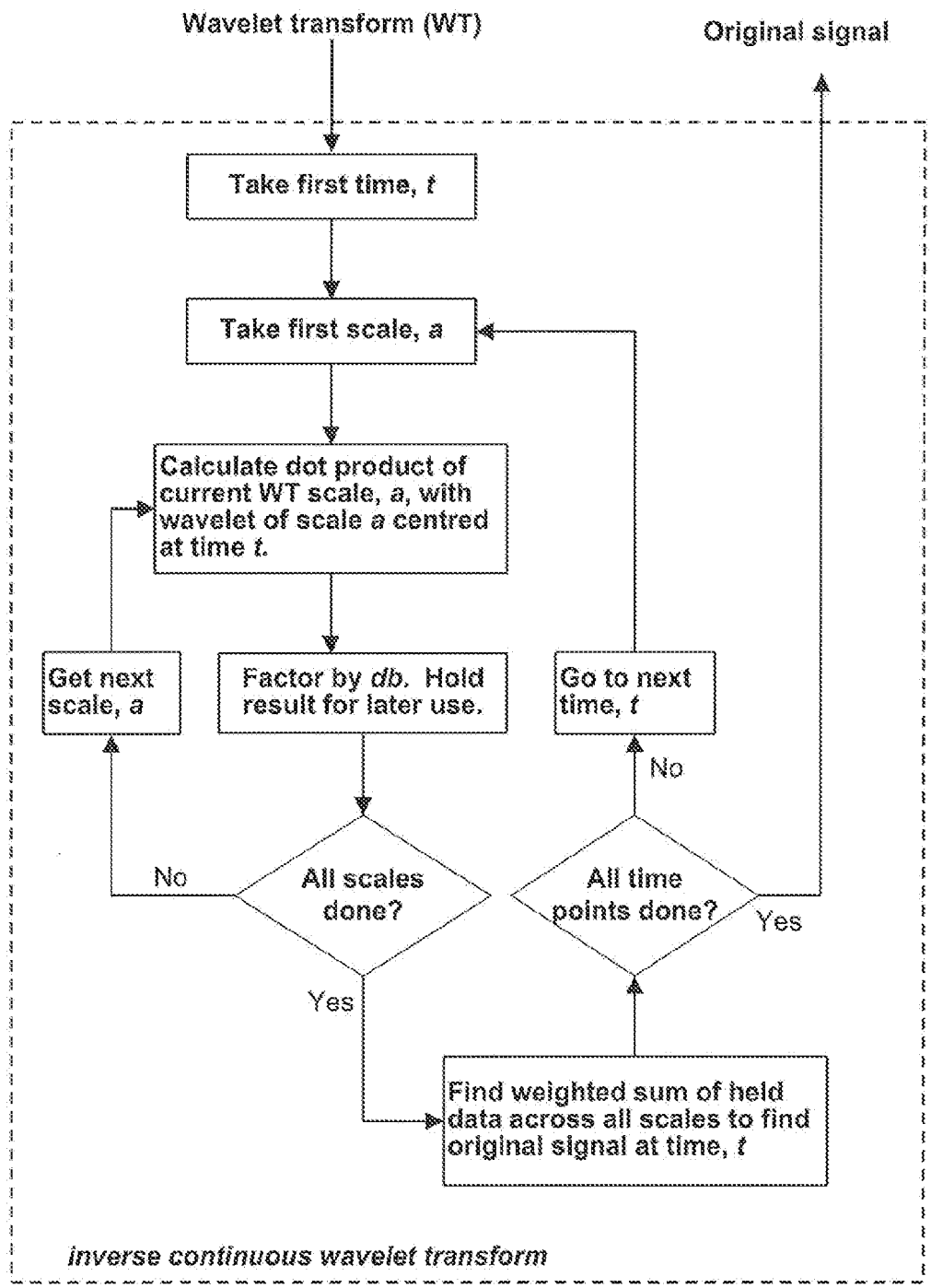
FIGS. 3(e) and 3(f) are flow charts of illustrative steps involved in performing an inverse continuous wavelet transform in accordance with embodiments.
Figure 3F:
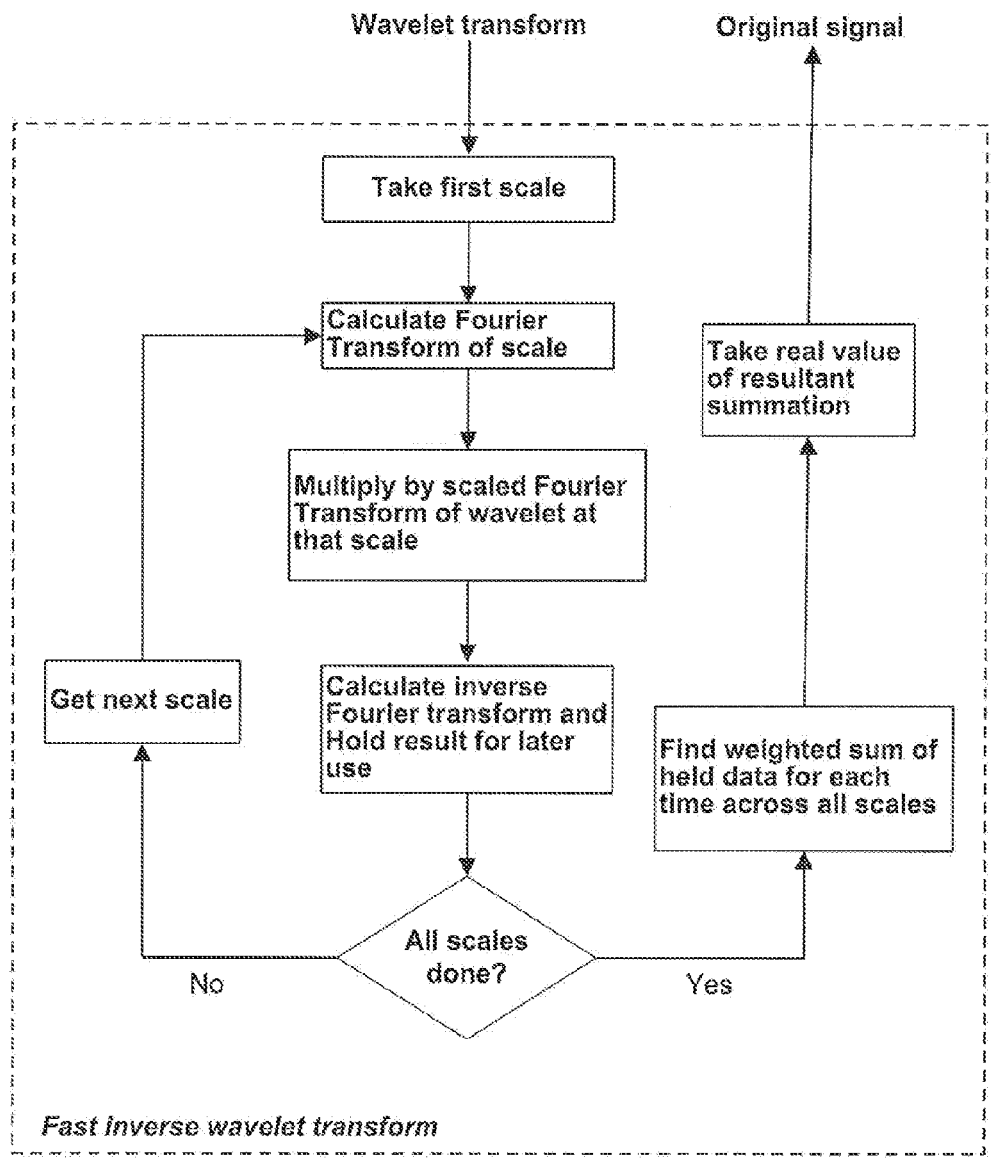

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
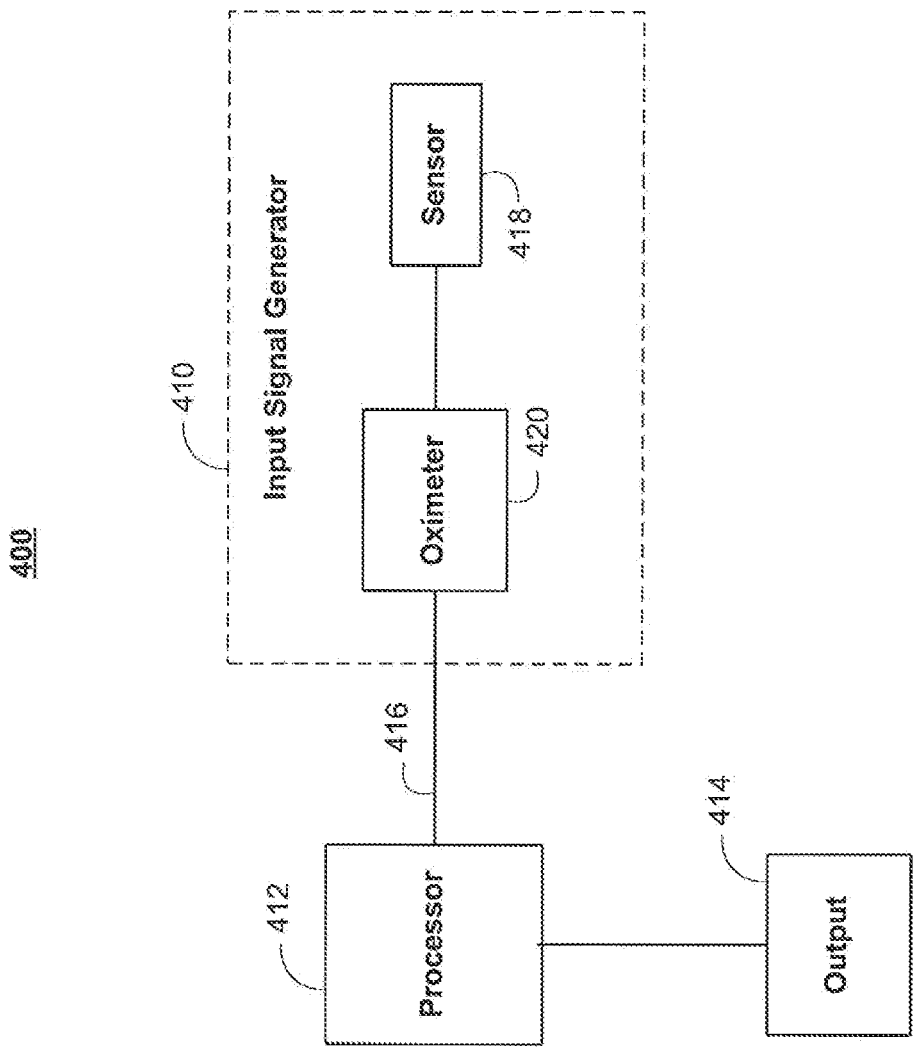
FIG. 4 is a block diagram of an illustrative continuous wavelet processing system in accordance with an embodiment.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Figure 5:
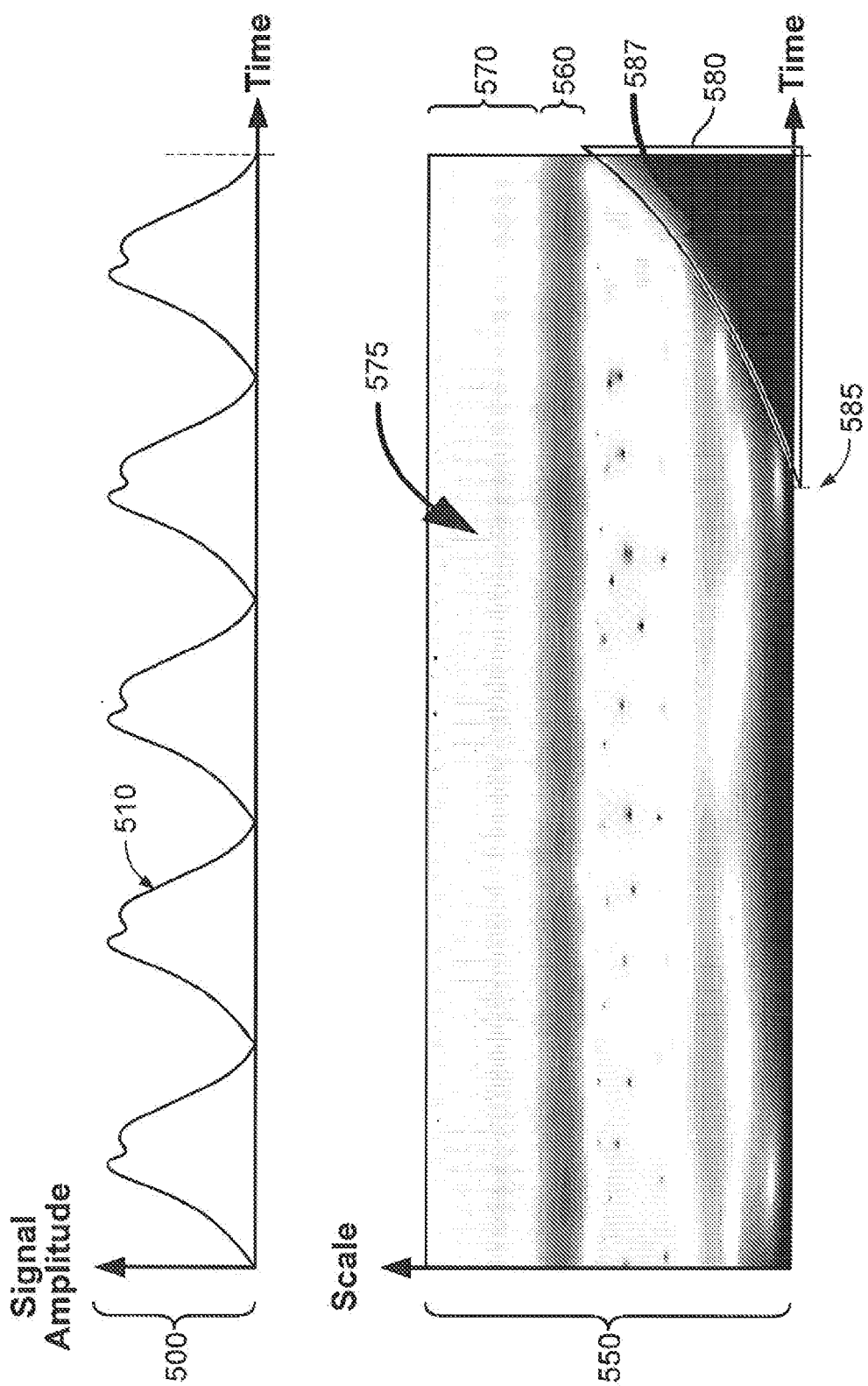
FIG. 5 illustrates a PPG signal and corresponding scalogram that may be obtained and/or generated from a pulse oximetry system in accordance with an embodiment.

FIG. 5 illustrates a PPG signal and corresponding scalogram that may obtained and/or generated from a pulse oximetry system, such as pulse oximetry system 10 (FIG. 1), in accordance with an embodiment. Plot 500 displays time on the horizontal axis ("x-axis") and amplitude values of PPG signal 510 on the vertical axis ("y-axis"). PPG signal 510 may be obtained from a patient, such as patient 40 (FIG. 2), using a sensor such as sensor 12 (FIG. 1). Alternatively, PPG signal 510 may be obtained by averaging or otherwise combining multiple signals derived from a suitable sensor array, as discussed in relation to FIG. 1. Plot 500 may be displayed using any suitable display device such as, for example, monitor 20 (FIG. 1), display 28 (FIG. 1), a PDA, a mobile device, or any other suitable display device. Additionally, plot 500 may be displayed on multiple display devices.

PPG signal 510 may exhibit an oscillatory behavior versus time, and may include several undulations of varying signal amplitude level and frequency. The size, shape, and frequency of the undulations of PPG signal 510 may be indicative of an underlying parameter or phenomenon that is to be detected or estimated. For example, PPG signal 510 may reflect the breaths or breathing cycle of a patient, such as patient 40 (FIG. 2), and/or may be used determine the respiration rate of the patient. PPG signal 510 may be a processed version of a preliminary PPG signal obtained by, for example, sensor 12 (FIG. 1). PPG signal 510 may contain erroneous or otherwise undesirable artifacts due to, for example, patient movement, equipment failure, and/or various noise sources, including thermal noise, shot noise, flicker noise, burst noise, and/or electrical noise caused by light pollution. These and other noise sources may be introduced, for example, through sensor 12 (FIG. 1), and/or cables 24, 32, and 34 (all of FIG. 1).

Scalogram 550 may be determined from, and correspond to, PPG signal 510. Scalogram 550 may be derived from PPG signal 510 using a processor such as processor 412 (FIG. 2) or microprocessor 48 (FIG. 2) of pulse oximetry monitor 14 (FIG. 1) to first compute the continuous wavelet transform of PPG signal 510. In scalogram 550, the horizontal axis denotes time and the vertical axis denotes scale. The darkness of the shading of a point in scalogram 550, denotes the relative energy value of the point. Scalogram 550 may include post-processing performed, for example, using user inputs 56 (FIG. 2), to set predetermined energy values if they are above and/or below predetermined thresholds. The predetermined energy and threshold values may be stored in ROM 52 (FIG. 2) and/or RAM 54 (FIG. 2). Alternatively, the energy and threshold values may not be predetermined, but rather, controlled by an operator, using, for example, user inputs 56 (FIG. 2) and a display such as monitor 26 (FIG. 1) or display 20 or 28 (both of FIG. 1).

Scalogram 550 may include distinct scale bands (i.e. ranges of scale values) including pulse band 560 and noise band 570. Pulse band 560 may contain an energy structure and energy values that reflect the pulse component of PPG signal 510. Pulse band 560 may be generally characterized by moderate to high energy values within the band and areas of lower energy at surrounding scale values. Noise band 570 may contain an energy structure and energy values that reflect general types of noise that may be present in PPG signal 510. For example, noise band 570 may include the effects of thermal noise, shot noise, flicker noise, burst noise, and/or electrical noise caused by light pollution. Noise band 570 may be generally characterized as having a less coherent energy structure and/or a lower energy level than pulse band 560.

Scalogram 550 may include wedge region 580. Wedge region 580 appears in a scalogram in the lower-right hand corner, and may represent a region of unresolved or partially resolved scalogram values. Wedge region 580 may form because future values of the underlying PPG signal, for example, PPG signal 510, are needed to fully resolve actual scalogram values. For example, in an embodiment, the infinite future values of the PPG signal may be needed to fully resolve scalogram values in wedge region 580, for example, when using the Morlet wavelet. Alternatively, rather than an infinite PPG signal, an operator may determine the degree of resolution needed to sufficiently "resolve" scalogram 550 for any practical application, and this information may be stored, for example, in ROM 52 (FIG. 2) or RAM 54 (FIG. 2). For example, an operator may determine the length of section of future signal values needed, for example, from PPG signal 510, so that the error between the true wavelet transform of the signal and the computed wavelet transform of the signal is acceptable for a given application, such as determining a patient respiration rate, oxygen saturation level, and/or respiration effort level. In an embodiment, the Morlet wavelet (or any other infinite-length wavelet) is computed using a section of an underlying signal that is of finite length, for example, having three standard deviations from the center of a Gaussian window forming part of the wavelet function, and longer or shorter sections of the underlying signal may also be used to resolve values in scalogram 500 in a practical manner. Typically, the length of the required section of future PPG values depends on the scale value for which the scalogram is being resolved, with larger scales (smaller values on the scale axis) requiring larger sections of the underlying signal, for example, PPG signal 510, to be resolved. Therefore, wedge region 580 may, in practice closely resemble a wedge shape, as shown in FIG. 5, but it may alternatively appear as a more or less regular shape. The energy values of scalogram 550 within wedge region 580 (i.e., energy values that have yet to be resolved to a sufficient degree) may be discontinuous from those outside of wedge region 580 and may include spurious and/or erroneous features, including noise, and/or other undesirable components. Therefore, in an embodiment, the displayed scalogram values in wedge region 580 may be set to low-energy predetermined values set by a user or operator prior to display, for example, on monitor 26 (FIG. 1) or display 20 or 28 (both of FIG. 1). For example, the scalogram values in wedge region 580 have been set to a constant low-energy value (denoted by dark black shading) to avoid obfuscating the fully resolved values of the scalogram present in resolved region 575. As described above, wedge region 580 may contain a significant number of erroneous values with spurious energy, and this is due to the apparent sharp discontinuity at the end of the underlying signal, for example, PPG signal 510. This is due to the wavelet being computed for the known part of the underlying signal and not for future values of the underlying signal, which produces the same scalogram as if the remaining values (i.e., future values) of the underlying signal are set to zero (producing an apparent large discontinuity).

A patient parameter may be determined based on interpolating, extrapolating, and/or extracting characteristics of scalogram 550. For example, the oxygen saturation, respiration rate, and/or the respiration effort level of a patient such as patient 40 (FIG. 2) may be determined from scalogram 550. The characteristics of scalogram 550 may additionally or alternatively be use to identity and/or filter noise or interference in PPG signal 510.

The discontinuous, spurious, erroneous and/or inaccurate energy values in wedge region 580 may typically degrade the overall quality of scalogram 550, and may thus degrade the detection and/or estimation of parameters, such as physiological parameters of patient 40 (FIG. 2). Alternatively, if scalogram values in wedge region 580 are ignored, then the extracted parameter values may be based on old and/or outdated scalogram data, which may lead to outdated and/or ineffective estimates of a parameter or parameters to be estimated, such as those of patient 40 (FIG. 2). For example, a patient respiration rate may be computed based on scalogram values occurring prior to time 585 if the wedge region of scalogram 550 is ignored. This approach may yield outdated parameter calculations if the time-rate of change of the patient respiration rate is sufficiently rapid.

Therefore, it may be desired to use wedge region 580 of the scalogram to compute parameter estimates or extract relevant parameters, while at the same time limiting the apparent discontinuities and erroneous energy values present in wedge region 580. For example, improved techniques for estimating the true scalogram values at various locations within wedge region 580 may be desirable. In an embodiment, an improved estimate of the scalogram value at a point, for example, point 587, in wedge region 580 may be determined from the scalogram energies in the immediate neighborhood of point 587. In this way, better estimates of the scalogram value at point 587 may be determined from known scalogram values outside of wedge region 580, as well as from previously estimated scalogram values within wedge region 580. Thus, in this manner, estimates of scalogram values in wedge region 580 are found by extending known information about a scalogram (i.e., scalogram 550) rather than an underlying signal (i.e., PPG signal 510). In an embodiment, a technique for estimating the scalogram value at point 575 may also rely on information from the physiological system producing the underlying signal, for example, PPG signal 510 or any other biosignal. For example, estimation of the scalogram value at point 587 may involve parameterization based on known techniques in the art, where parameters may depend on past and/or current characteristics of patient 40 (FIG. 2), room conditions such as temperature and lighting, template matching with existing biological models, and/or on any other suitable technique.

Although the techniques disclosed herein are described in terms of PPG signal 510, the disclosed techniques may be applied to any other suitable signal. For example, the disclosed techniques may be applied to other biosignals including transthoracic impedance signals, and/or capnograph signals. Further, PPG signal 510 or any other related signal may be obtained from a source other than pulse oximeter system 10 (FIG. 1). For example, PPG signal 510 may be obtained from another type of medical device or from non-medical devices including a general signal oscilloscope, signal generator, and/or waveform analyzer. PPG signal 510 may be a simplified embodiment of a PPG signal, or other type of signal, measured in practice. The techniques disclosed herein may be applied to signals that, for example, have more or less frequent undulations than PPG signal 510, time-variant mean amplitude values, noise patterns, and/or discontinuities. The techniques described herein may be applied to PPG signals that do not resemble the time-varying pattern of PPG signal 510 shown in FIG. 5.

Figure 6A:
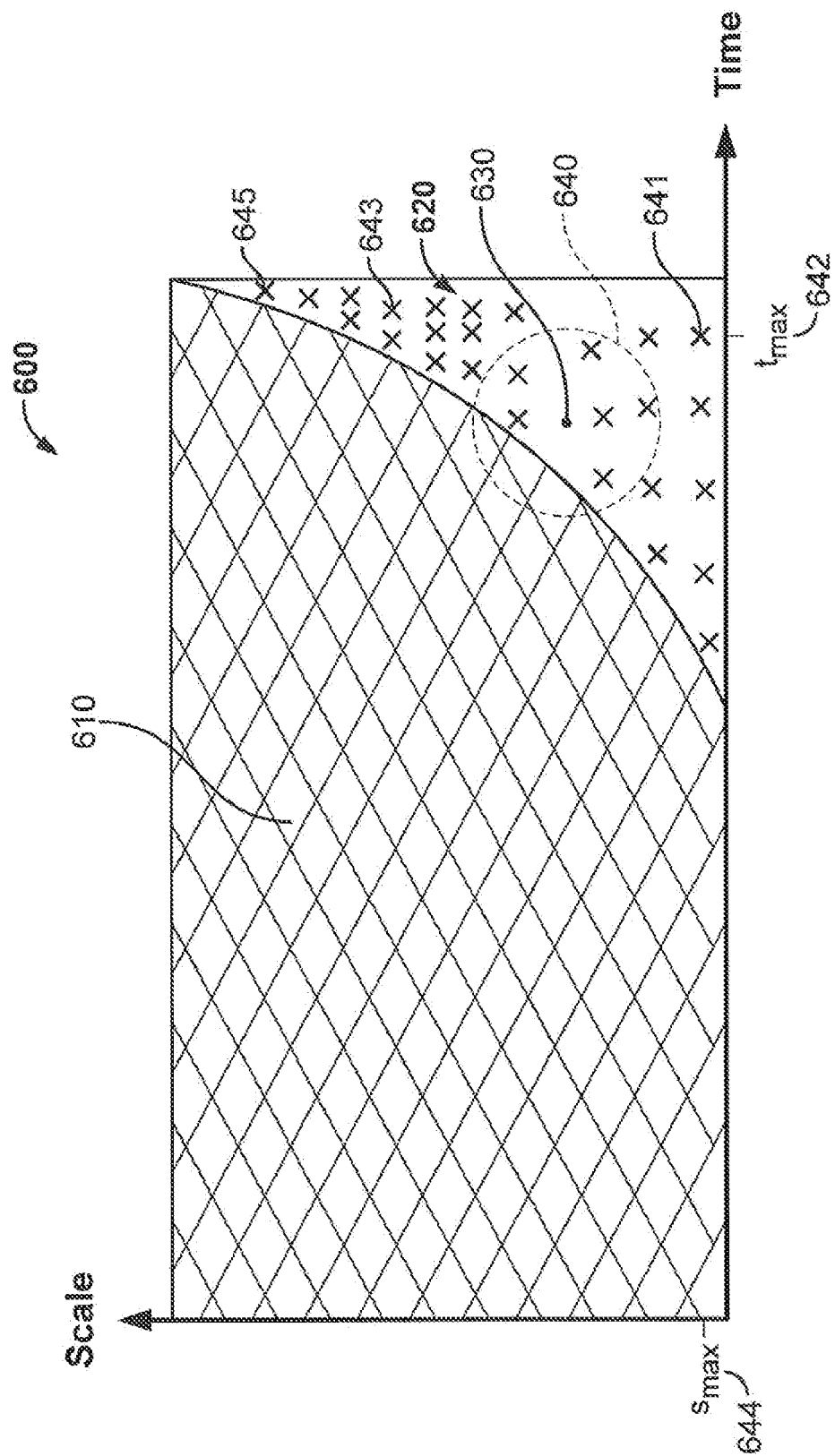
FIGS. 6A-B are simplified illustrations of scalograms and techniques that may be used to estimate (or otherwise determine) scalogram values in a wedge region in accordance with an embodiment.

FIG. 6A is a simplified illustration of a scalogram and technique that may be used to estimate or otherwise determine scalogram values in a wedge region. Scalogram 600 includes resolved region 610 and wedge region 620, which may correspond to resolved region 575 (FIG. 5) and wedge region 580 (FIG. 5), respectively, of scalogram 500 (FIG. 5). An improved technique to determine scalogram values in wedge region 620 will now be summarized, and more detailed embodiments and features of the technique will be described in relation to FIGS. 7-10. First, a number and a set of locations within wedge region 620 may be determined for which scalogram estimates are to be made. For example the points denoted by ", in wedge region 620 may denote the location and number points for which scalogram estimates are to be performed. Next, a point within wedge region 620, for example, point 630, may be selected, and an estimate of the true (i.e., actual) scalogram value at point 630 may be determined based on scalogram values contained within vicinity region 640. As shown in FIG. 6, vicinity region 640 may encompass both resolved scalogram values (i.e., from resolved region 610) and previously estimated scalogram values (i.e., contained within wedge region 620), depending on the location of point 630 and the size (and shape, as described below) of vicinity region 640. Vicinity region 640 may also include points for which no scalogram estimates have been taken. Such points may be ignored, for example, set to the value zero or the value "undefined," in computing an estimate of the scalogram value at point 630.

Next, a new point in wedge region 620 may be selected, the vicinity region correspondingly moved to match the location of the newly selected point, and the estimation process described above may then be used to estimate the true value of a scalogram at the new point using the techniques described above. This estimation process may repeat until estimates of the true value of the scalogram have been estimated at a sufficient number of points in wedge region 620. For example, the process may repeat until an estimate has been determined at each point marked with an " in wedge region 620. In an embodiment, multiple passes of the estimation technique described herein may be performed, and some or all of the points marked with an " in wedge region 620 may be estimated more than once, for example, during more than one pass. This approach may be advantageous in exploiting scalogram estimates in a later pass than were not available in an earlier pass or for iteratively refining scalogram estimates. The number of passes performed may depend on computational resources available, the level of desired estimation accuracy, and/or on the allowable time-delay in estimating scalogram values with wedge region 620. As shown in FIG. 6, not all points in wedge region 620 are directly estimated (e.g., in an embodiment, only those points marked with an " are estimated). Estimates of the true value of the scalogram for these points may be derived instead by interpolating neighboring estimates (e.g., by interpolating estimates of the scalogram value taken at points marked with an " in scalogram 600).

Figure 6B:
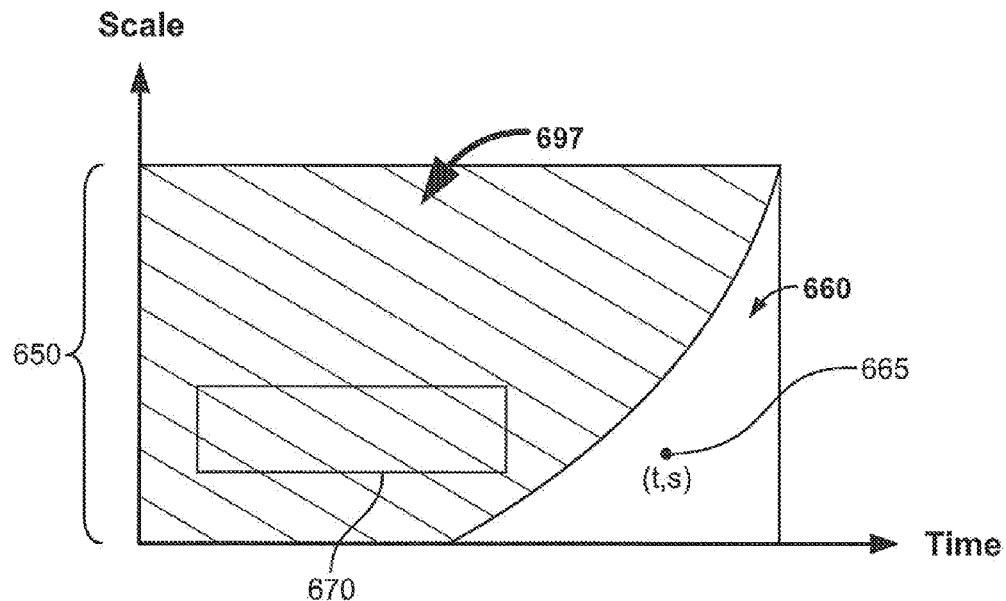
Figure 6B:
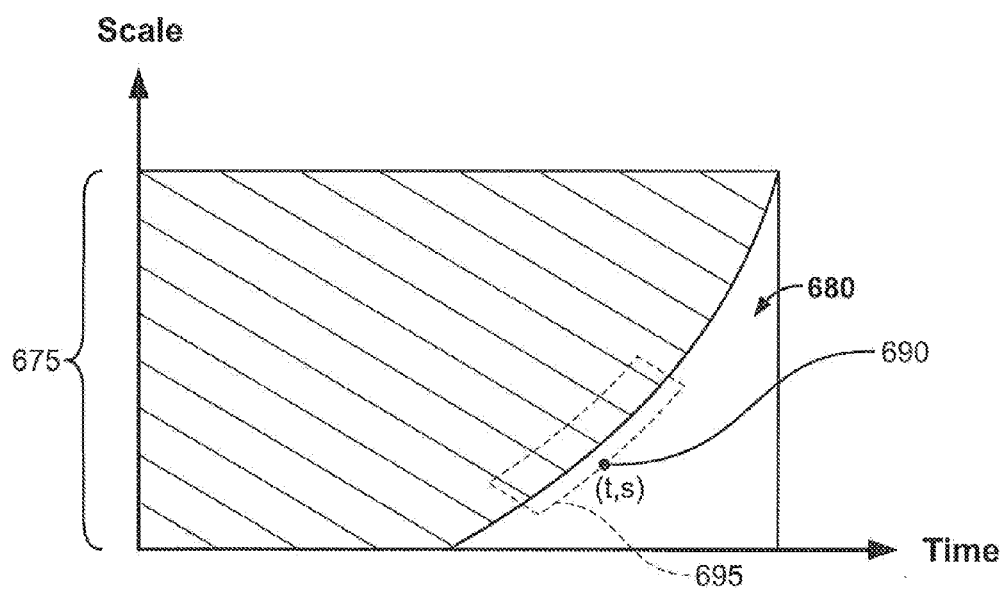

In an embodiment, vicinity region 640 may be circular, as shown in FIG. 6. However, the estimation scheme disclosed herein can be used with a vicinity region of any suitable shape and/or size, including for example, any polygonal shape, regular geometric shape, or an arbitrary shape. In an embodiment, the shape of vicinity region 640 may depend on the location of the point to be estimated, for example, point 630, within the vicinity region and/or on the shape of the curved border where the wedge region, for example, wedge region 620, meets the resolved region, for example, resolved region 610. For example, the shape of vicinity region 695 (FIG. 6B) is shaped to conform to the shape of the curved border where wedge region 680, meets resolved region 697.

In an embodiment, the point at which the scalogram value is to be estimated, for example, point 630, may not be centered within the corresponding vicinity region, but rather, may be located at any other position within, on the border of, or outside the corresponding vicinity region. For example, scalogram 650 (FIG. 6B) illustrates an embodiment for which the vicinity region, that is, vicinity region 670 (FIG. 6B), does not include the estimation point, that is, point 665 (FIG. 6B). Alternatively, scalogram 675 illustrates an embodiment for which the vicinity region, that is, vicinity region 695 (FIG. 6B), includes the point to be estimated, that is, point 690 (FIG. 6B), on the border of the vicinity region.

Figure 7:
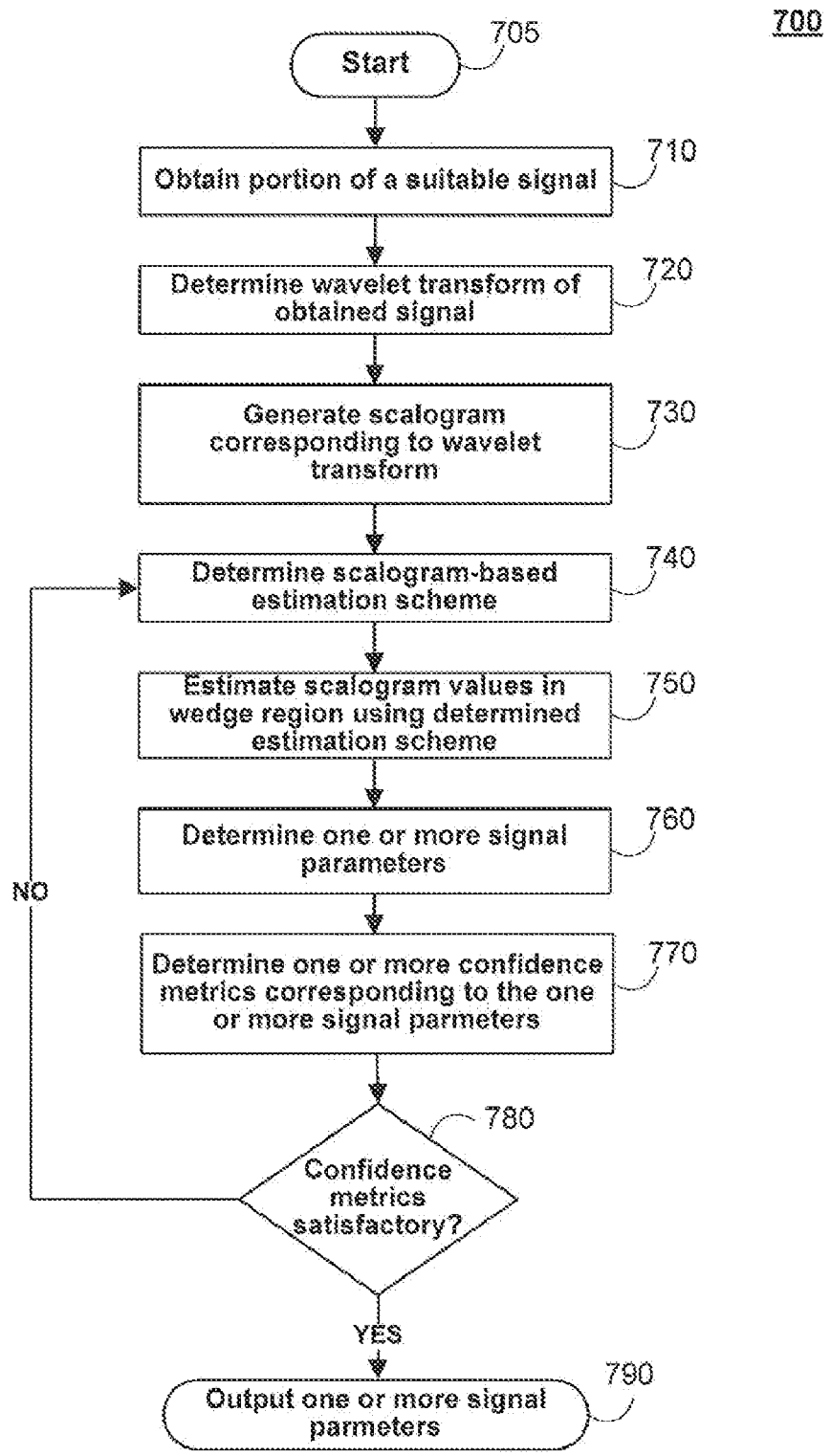
FIG. 7 depicts an illustrative process for estimating scalogram values in a wedge region in accordance with an embodiment.

FIG. 7 depicts an illustrative process for estimating scalogram values in a wedge region, for example, wedge region 620 (FIG. 6B) in accordance with an embodiment. Process 700 may start at step 705. At step 710, a portion of a suitable signal may be obtained, for example, using pulse oximetry system 10 (FIGS. 1 and 2) or system 400 (FIG. 4). The signal obtained at step 710 may be a PPG signal and/or any suitable biosignal. At step 720, a continuous wavelet transform of the signal obtained at step 710 may be obtained. At step 730, the scalogram of the continuous wavelet transform may be generated or otherwise obtained. For example, the scalogram of the continuous wavelet transform may be generated or obtained using a processor such as processor 412 (FIG. 4) or microprocessor 48 (FIG. 2) and the computed scalogram may be displayed on a monitor such as monitor 26 (FIG. 1) or display 20 or 28 (both of FIG. 1).

At step 740, an estimation scheme for estimating scalogram values in a wedge region, such as wedge region 620 (FIG. 6A), may be determined. For example, various parameters of the estimation scheme may be determined at step 740. The parameters of the estimation scheme may be set manually by an operator using user inputs 56 (FIG. 2), automatically by pulse oximetry monitor 14 (FIG. 1), or through a combination thereof. In an embodiment, parameters of the estimation scheme may depend on the biological characteristics of patient 40 (FIG. 2). At step 750, scalogram values in the wedge region may be estimated. For example, scalogram values may be estimated using the estimation scheme determined at step 740, and may be performed by pulse oximetry monitor 14 (FIG. 1) using processor 412 (FIG. 2) or microprocessor 48 (FIG. 2). The estimated values of the scalogram may be displayed on a monitor or display such as monitor 26 (FIG. 1) or display 20 or 28 (both of FIG. 1). Step 750 may produce a "complete" scalogram, where the complete scalogram is the scalogram obtained at step 730 with energy values in the wedge region, for example, wedge region 620 (FIG. 6A), replaced by the estimated scalogram values obtained at step 750.

At step 760, one or more signal parameters may be determined based on the complete scalogram obtained at step 750. For example, signal parameters corresponding to the biological characteristics of patient 40 (FIG. 2) may be determined, including oxygen saturation, respiration rate, and/or respiration effort. In an embodiment, noise parameters and/or noise characteristics of the signal obtained at step 710 may be determined at step 760. For example, noise parameters may be determined by applying one or more filters or image processing algorithms to the complete scalogram, by using template matching, averaging, and/or any other suitable technique. In an embodiment, noise may be removed from the complete scalogram or directly from the signal obtained at step 710, based on the determined noise parameters and/or noise characteristics.

At step 770, one or more confidence metrics may be determined, where each confidence metric corresponds to a measure of the accuracy and/or reliability of a parameter (or parameters) determined at step 760. The one or more confidence metrics may be determined using, for example, using processor 412 (FIG. 4) or microprocessor 48 (FIG. 2). In an embodiment, each confidence metric may represent the statistical probability (or, for example, the empirically determined fraction of time) that a parameter determined at step 760 is correct to within a specified threshold. Alternatively, a confidence indicator may represent a degree of confidence, measured on any suitable scale, that a parameter has been correctly determined, and may be measured, for example, by a mean square error criterion. A probability or confidence indicator may be determined using, for example, Bayesian or Neyman-Pearson statistical techniques computed in processor 412 (FIG. 4), historical or trend data preloaded or otherwise available in monitor 14 (FIG. 1), patient specific medical information provided to monitor 14 (FIG. 1), user inputs 56 (FIG. 2), or any other suitable technique. At step 780, the one or more confidence metrics determined at step 780 may be compared thresholds or any other suitable test, for example, including a binary test. In an embodiment, the one or more confidence metrics may be tested to determine if they satisfy a constraint set. If the one or more confidence metrics are determined to be valid (for example, if the one or more confidence metrics satisfy the constraint set), then process 700 may proceed to step 790. If however, at least one of the tests carried out at step 780 fails (for example, if a binary test fails), then process 700 may return to step 740. At step 740, process 700 may reset parameters associated with the estimation scheme, for example, to improve the performance of the estimation scheme. For example, process 700 may increase the number of estimation points, increase the complexity (and therefore performance) of the estimation algorithm, or change the size and/or shape of the vicinity region, as described above.

In process 700, steps 770 and 780 are optional, and if included, may allow for iterative improvements in the quality of the one or more parameters determined at step 760. If, however, steps 770 and 780 are not included in an embodiment of process 700, then process 700 may proceed to step 790 directly from step 760. In either case, at step 790, the one or more signal parameters determined at step 760 may be output. For example, the signal parameters may be output to a display such as monitor 26 (FIG. 1) or display 20 or 28 (both of FIG. 1), through an audible message provided through a speaker such as speaker 22 (FIG. 2), through a written printout, or through a combination of some of these and other suitable techniques.

Figure 8:
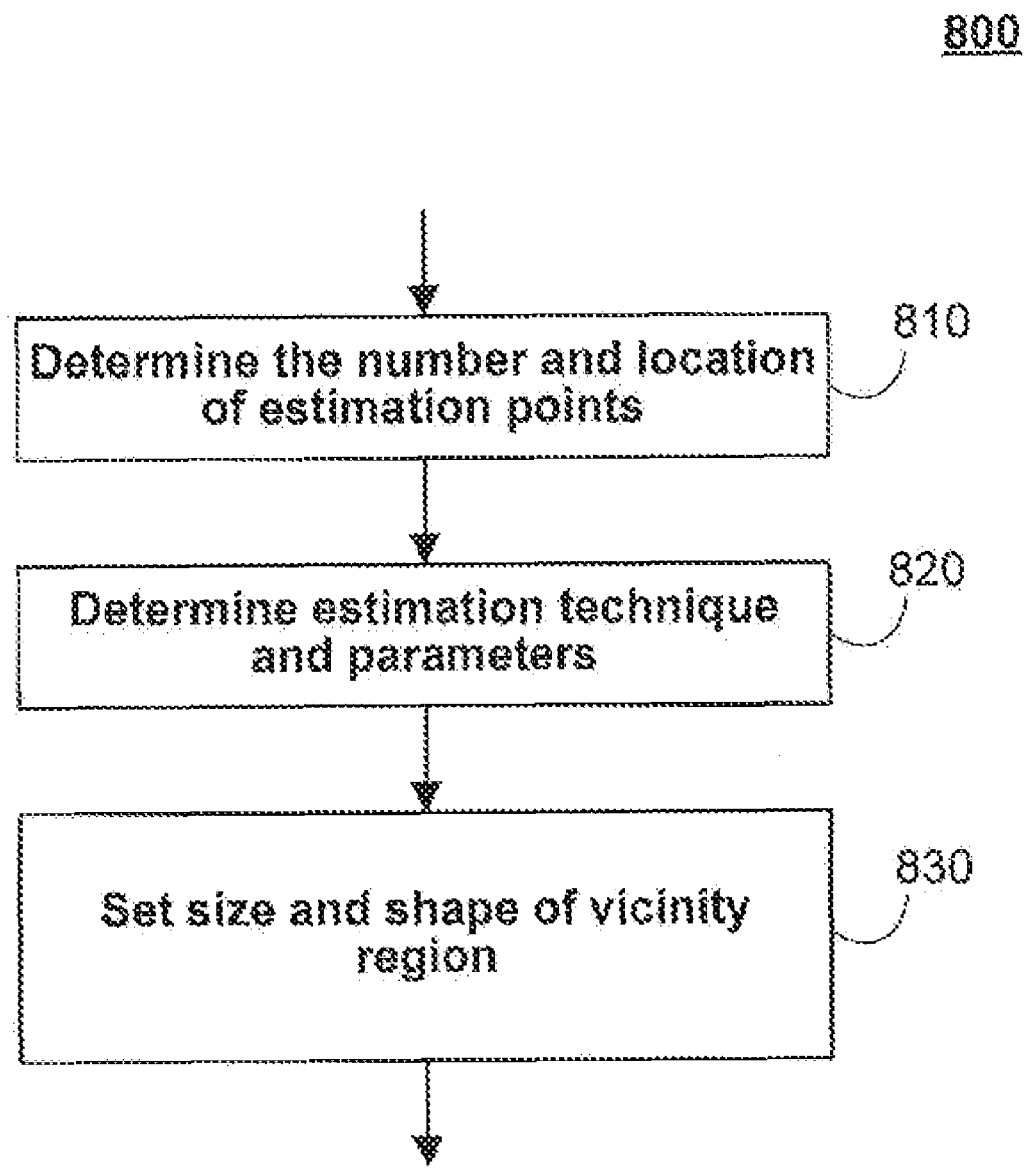
FIG. 8 depicts an illustrative process for determining a scalogram-based estimation scheme in accordance with an embodiment.

FIG. 8 depicts an illustrative process for determining a scalogram-based estimation scheme in accordance with an embodiment. Process 800 may be a further embodiment of step 740 of process 700 (both of FIG. 7). At step 810, the number and location of estimation point within the wedge region, for example, wedge region 580 (FIG. 5), may be determined. The number and location of estimation points may be based on specific system and patient parameters and/or may depend on tunable parameters that can be controlled by an operator, for example, using user inputs 56 (FIG. 2) to tune parameters viewable on a display such as monitor 26 (FIG. 1) or display 20 or 28 (both of FIG. 1). If the number and location of estimation points are chosen statistically, they may be chosen based on a density criterion, specified, for example, in terms of a number of estimation points per scale and/or time. The desired density may be tuned using user inputs 56 (FIG. 2). Alternatively or additionally, the number and location of estimation points may be determined based on factors including the desired estimation quality, the computation resources available, and/or the maximum tolerable computational delay. The number and location of estimation points chosen at step 810 may be chosen as to provide estimates for the entire wedge region, for example, wedge region 580 (FIG. 5), or may be chosen relatively sparsely. In the latter case, interpolative or other smoothing techniques may be used to create the completed scalogram based on the estimated scalogram values.

At step 820, an estimation technique, including related parameters, may be determined. The estimation technique may be used to combine, weigh, interpolate, or otherwise parse data samples contained within the vicinity circle, for example, vicinity circle 640 (FIG. 6A), to determine estimates of the true scalogram value at each point determined at step 810. Any suitable estimation technique may be used. For example, two-dimensional surface interpolation may be used, or extrapolation techniques from the full resolved region, for example, fully resolved region 610 (FIG. 6A) may be used. The vicinity circle, for example, vicinity circle 640 (FIG. 6A), may use sample points in both the fully resolved region and the wedge region, for example, wedge region 620 (FIG. 6A), to determine an estimate of the true value of the scalogram at a point, for example, point 630 (FIG. 6A). In an embodiment, an estimate at a point, for example, point 630 (FIG. 6A) may be made, at least partially, by weighing data points within the vicinity circle according to degree to which each data point is resolved. For example, data points that are more fully resolved (i.e., located further to left in a scalogram such as scalogram 550 (FIG. 5) may contribute more to a final estimate of the scalogram value at the estimation point compared to data points that are only partially resolved (i.e., located further to the right in a scalogram such as scalogram 550 (FIG. 5). Further, to estimate the value of the scalogram at a point such as point 630 (FIG. 6A), a surface model may be built or referenced, and a two-dimensional functional approximation to the surface model may be used, possibly in addition to other techniques, to estimate the value of the scalogram at the desired point.

At step 830, the size and shape of the vicinity region may be determined. For example, vicinity region 640 (FIG. 6A) may be used to estimate scalogram point 630 (FIG. 6A), vicinity region 670 (FIG. 6B) may be used to estimate scalogram point 665 (FIG. 6B), and vicinity region 695 (FIG. 6B) may be used to estimate point 690 (FIG. 6B). The size and shape of the vicinity region may be set based on template matching preexisting models of scalogram surfaces, on characteristics of a biological parameter to be estimated, and/or on patient characteristics, in addition to any other suitable factor.

Figure 9:
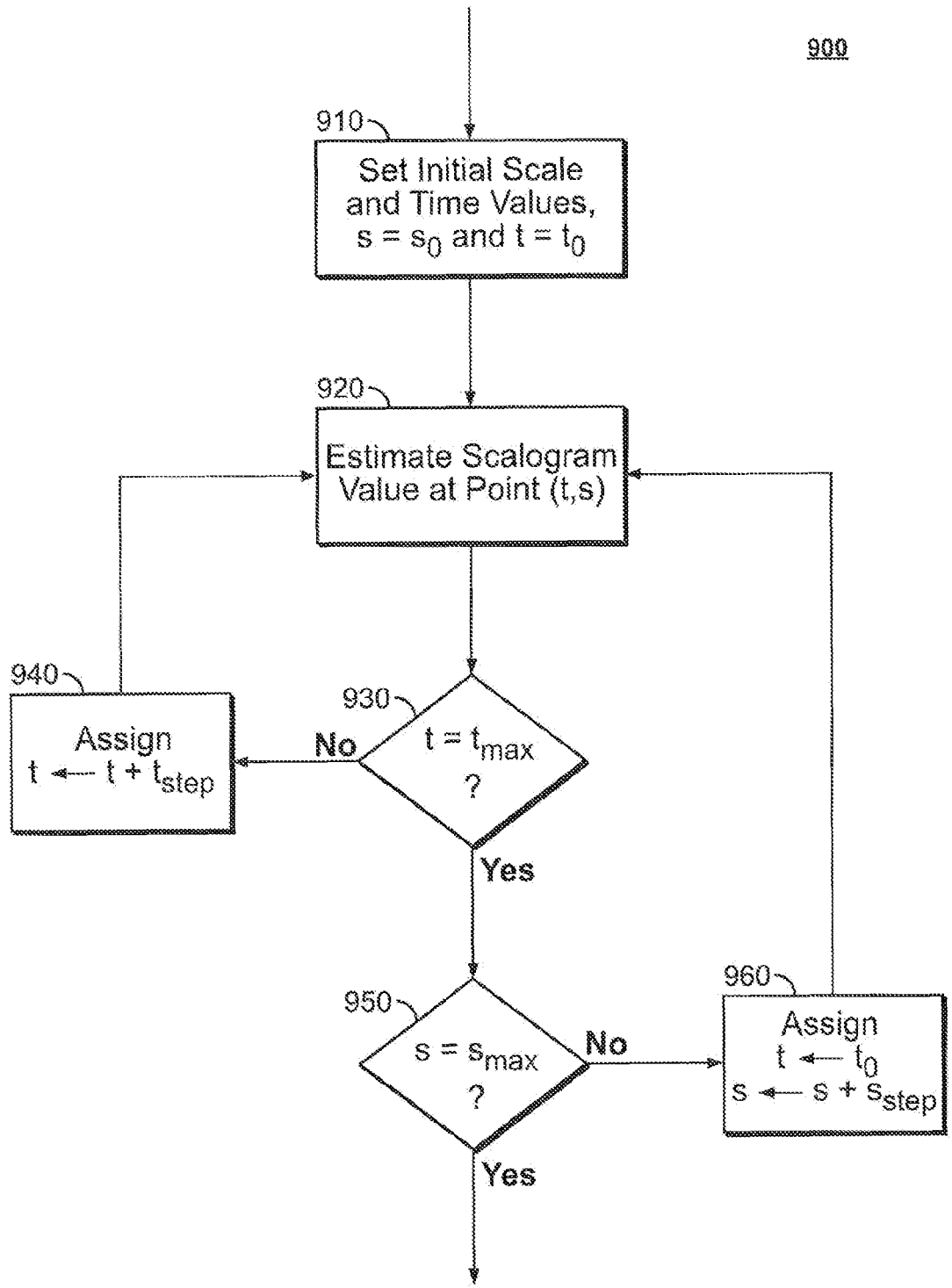
FIG. 9 depicts an illustrative process for estimating scalogram values in a wedge region using a determined estimation scheme, in accordance with an embodiment.

FIG. 9 depicts an illustrative process for estimating scalogram values in a wedge region, for example, wedge region 620 (FIG. 6A) using a determined estimation scheme, for example, determined at step 740 of process 700 (both of FIG. 7), in accordance with an embodiment. Process 900 may correspond to a further embodiment of step 750 of process 700 (both of FIG. 7). Process 900 may be used to iteratively estimate scalogram values in a structured grid pattern. For example, process 900 may be used to estimate the scalogram value at each grid point marked with an " in wedge region 620 of scalogram 600 (both of FIG. 6A). In an embodiment, process 900 may first estimate the value of the scalogram at point 645 (FIG. 6A), and then iteratively estimate scalogram values, proceeding from left to right within each row of wedge region 620 (FIG. 6A).

At step 910, initial scale and time values may be set. In an embodiment, the initial scale and time values may be set to correspond to one of the estimation points determined at step 740 of process 700 (FIG. 7) or step 810 of process 800 (FIG. 8). For example, an initial scale value may be set to the point $s=s_0$ and an initial time value may be set to a point $t=t_0$, where $s_0$ and $t_0$ denote a starting point in a wedge region, for example, point 645 in wedge region 620 (both of FIG. 6A).

At step 920, process 900 may estimate the true value of the scalogram at the point selected at step 910. For example, if point 645 (FIG. 6A) is selected at step 910, then process 900 may estimate the true value of the scalogram at this point at step 920. Process 900 may use any suitable technique to estimate the scalogram value at step 920, including any of the techniques described at step 820 of process 800 (both of FIG. 8). At step 930, the current value of the time scale, t, may be compared to a maximum time value, $t_{max}$. For example, as shown in FIG. 6A, time 642, that is, a time equal to $t_{max}$, may represent the maximum (i.e., most recent) time scale value for which the scalogram is to be estimated. If the value of t is less than $t_{max}$, then process 900 may proceed to step 940. At step 940, the value of t may be incremented to the next value for which the scalogram is to be estimated. In an embodiment, the estimation points are placed in regular structure (for example, as shown by the " marks in wedge region 620 of FIG. 6A), and in this case, the value of $t_{max}$ be incremented by a constant value $t_{step}$, where $t_{step}$ is a positive number. If, at step 930, the value of t equals the value of $t_{max}$, then process 900 may proceed to step 950. At step 950, the value of s may be incremented to the next value for which the scalogram is to be estimated. For example, the value of s may first be compared to a maximum value, $s_{max}$, shown in FIG. 6A as scale value 644. If the value of s is equal to the value of $s_{max}$, then $t=t_{max}$ and $s=s_{max}$, indicating that the scalogram estimation procedure has completed estimating all scalogram points, determined, for example, at step 810 of process 800 (both of FIG. 8). For example, in FIG. 6A, the estimation process may have enumerated all grid points with the last placed point being point 641 (FIG. 6A). If at step 950, the value of t is determined to be $t_{max}$, then process 900 may have finished estimated scalogram values along a particular row of grid points that is not the last row. For example, process 900 may be at point 643 (FIG. 6A). In this case, process 900 may move to the first point on the next row, by setting $t=t_0$ and by incrementing the value of s by $s_{step}$. The value of $t_0$ may depend on the current value of s, and may conform to the shape of the wedge region, for example, wedge region 620 (FIG. 6A).

The process described above is merely illustrative and various alternations and changes could be made to the techniques described above. For example, grid points may be determined using a non-regular structure. In this case, the iterative estimation scheme described above, and in particular steps 930, 940, 950, and 960 of process 900 could be readily modified so that the values of $t_{step}$ and $s_{step}$ depend on the particular locations of grid points within a wedge region, for example, wedge region 620 (FIG. 6A). Similarly, the process described above performs inner iterations across time, but could be readily modified so that inner iterations are performed across scale values or any other suitable regular or irregular dimension.

Figure 10:
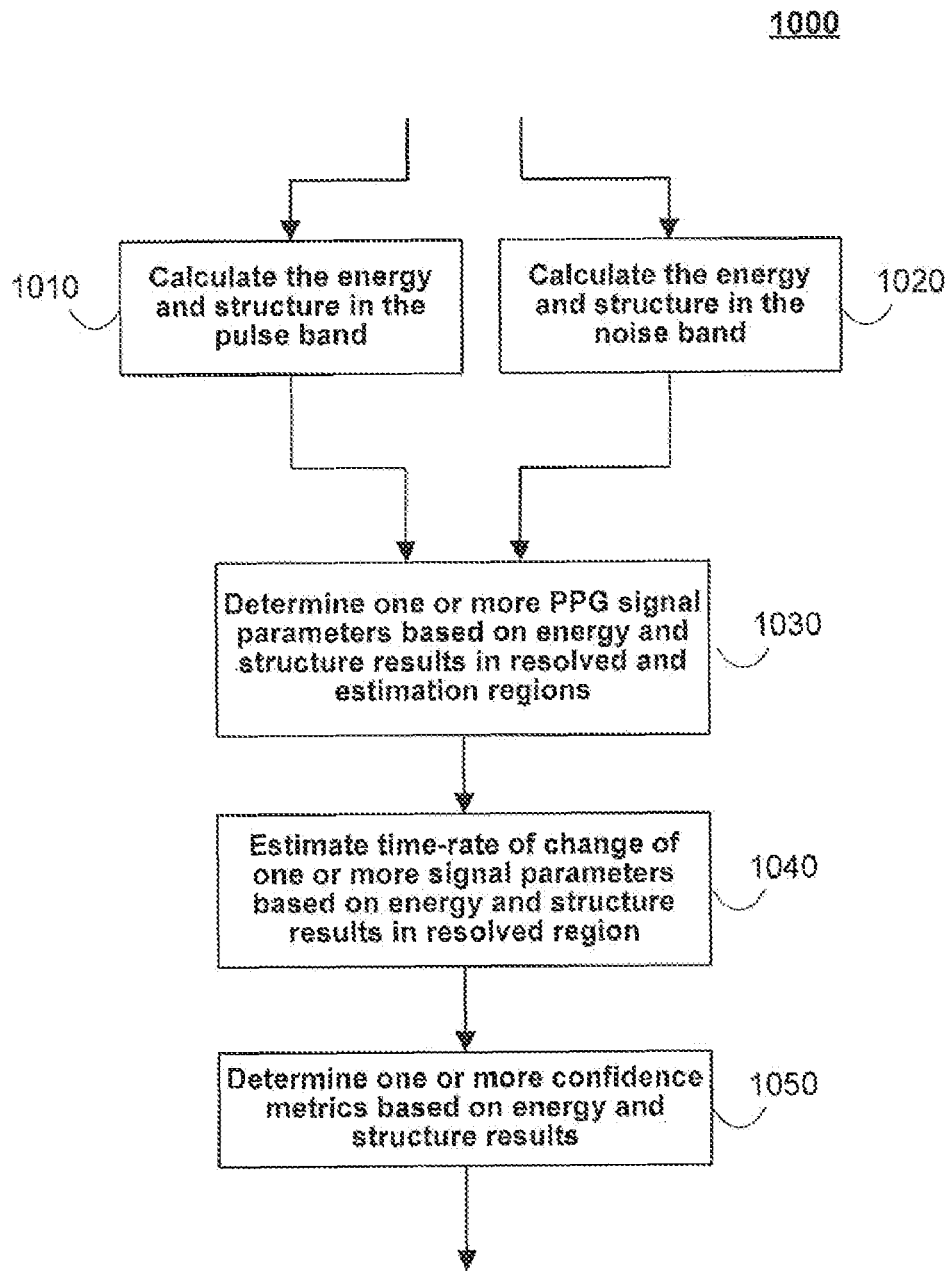
FIG. 10 depicts an illustrative process for determining one or more signal parameters and determining one or more confidence metrics from a scalogram, in accordance with an embodiment.

FIG. 10 depicts an illustrative process for determining one or more signal parameters and determining one or more confidence metrics in accordance with an embodiment. Process 1000 may represent a further embodiment of steps 760 and 770 of process 700 (all of FIG. 7). At step 1010, the energy values and energy structure in a scalogram pulse band, for example, pulse band 560 of scalogram 550 (both of FIG. 5) may be calculated. Energy values may be calculated by averaging the energy densities of a scalogram, such as scalogram 550 (FIG. 5), within a given time-window or through any other suitable technique. For example, energy may be calculated by averaging the energy density only over those energy values below a certain percentile threshold in pulse band 560 (FIG. 5), or by averaging only the minimum or maximum values at each time instant. Alternatively, the energy structure in pulse band 560 (FIG. 5) may be calculated by recording the presence of features within a given time-window such as the number of and frequency of repeated patterns, the presence of high energy regions followed by low energy regions, and/or any other suitable characteristics.

At step 1020, the energy values and energy structure in a noise band, for example, noise band 570 (FIG. 5) may be calculated. Energy values may be calculated by averaging the energy densities of a scalogram, such as scalogram 550 (FIG. 5), for example, within a given time-window and/or through any other suitable scheme. For example, energy may be calculated by averaging the energy density only over energy values below a certain percentile threshold in noise band 570 (FIG. 5), or by averaging only the minimum or maximum values at each time instant. Alternatively, the energy structure in noise band 570 (FIG. 5), may be calculated by recording the presence of features within a given time-window such as the number of and frequency of repeated patterns, the presence of high energy regions followed by low energy regions, and/or any other suitable characteristics.

At step 1030, one or more signal parameters may be determined from the energy and structure results calculated at steps 1010 and 1020. For example, a respiration rate, oxygen saturation level, and/or respiration effort level of a patient such as patient 40 (FIG. 2) may be determined. To determine the one or more signal parameters, curve fitting may be performed on plots of energy values, energy structural characteristics, signal-to-noise levels, as well as on any other plots or other data types that may have been determined at step 1010 and 1020. The curve fitting may be done using linear least-squares fitting of data, higher-order interpolative techniques, or any other suitable technique. Parameterization and/or curve fitting can be performed, for example, by processor 412 (FIG. 4) or microprocessor 48 (FIG. 2), and may additionally depend on parameters entered by a user through user inputs 56 (FIG. 2). At step 1030, the one or more signal parameters may be determined based on current data as well as from past data (e.g., generated in previous iterations of process 1000). Such past data may be stored in, for example, ROM 52 (FIG. 2) and/or RAM 54 (FIG. 2).

At step 1040, one or more confidence metrics may be determined corresponding to the signal parameters determined at step 1030. For example, a confidence metric may be determined based on the energy and structure results determined at step 1010 and/or 1020, and/or based on current and/or past data from signal-to-noise level plots. Alternatively or additionally, confidence metrics may be determined using tabulated figures or merit or through any other suitable scheme. Each confidence metric may be represented by a number from 0 to 100, where a larger number indicates a higher confidence level. Alternatively or additionally, any suitable parsing, combining, or weighing strategy may be used to combine the energy and/or structure results of steps 1010 and 1020 to determine the one or more confidence metrics. For example, maximum-likelihood techniques may be used to combine data and Neyman-Pearson combining techniques may be used when the prior probability of a signal quality decrease event is unknown. At step 1040, the one or more confidence metrics may be determined based on current data as well as from past data (e.g., generated in previous iterations of process 1000). Such past data may be stored in, for example, ROM 52 (FIG. 2) and/or RAM 54 (FIG. 2).

It will be understood that, while the above disclosure is made in the context of a medical signal processing application (i.e., based on one or more PPG signals generated by a pulse oximetry system), the features of the present disclosure may be applied in the context of any signal processing application and may be applied to any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

It will also be understood that the above method may be implemented using any human-readable or machine-readable instructions on any suitable system or apparatus, such as those described herein.

The foregoing is merely illustrative of the principles of this disclosure and various modifications can be made by those skilled in the art without departing from the scope and spirit of the disclosure. The following claims may also describe various aspects of this disclosure.

What is claimed is:

1. A method for processing a scalogram to estimate one or more energy values in a wedge region of the scalogram, the method comprising:
   receiving a signal; and
   using processing equipment for:
      transforming the signal based at least in part on a continuous wavelet transform;
      generating the scalogram based at least in part on the transformed signal;
      estimating the one or more energy values in the wedge region of the scalogram based at least in part on an estimation scheme;
      determining one or more signal parameters of the signal based at least in part on the one or more estimated energy values; and
      outputting the determined one or more signal parameters to an output device.

2. The method of claim 1, wherein estimating the one or more energy values comprises:
   determining a plurality of estimation points and a set of locations corresponding to the plurality of estimation points in the wedge region of the scalogram;
   determining a set of estimation parameters corresponding to the estimation scheme; and
   determining a size and shape of a vicinity region.

3. The method of claim 2, wherein the determined size and shape of the vicinity region is based, at least in part, on one or more characteristics of the one or more signal parameters.

4. The method of claim 2, wherein the determined size and shape of the vicinity region is based, at least in part, on one or more characteristics of a patient.

5. The method of claim 1, wherein the signal comprises a photoplethysmograph (PPG) signal received from a sensor.

6. The method of claim 1, wherein the one or more signal parameters comprises a patient oxygen saturation level.

7. The method of claim 1, wherein the signal parameter comprises a patient respiration rate.

8. The method of claim 1, wherein the method further comprises:
   determining one or more confidence metrics based at least in part on the one or more estimated energy values; and
   determining if the one or more confidence metrics satisfy a constraint set.

9. The method of claim 8, wherein determining the one or more confidence metrics comprises:
   determining energy values and energy structure in a pulse band of the scalogram; and
   determining energy values and energy structure in a noise band of the scalogram.

10. The method of claim 1, wherein the estimate of at least one energy value in the one or more estimated energy values is based, at least in part, on a set of resolved energy values in a resolved region of the scalogram and a set of estimated energy values in the wedge region of the scalogram.

11. A system for processing a scalogram to estimate one or more energy values in a wedge region of the scalogram, the system comprising:
   a sensor capable of generating a signal; and
   one or more processors coupled to the sensor, wherein the one or more processors are capable of:
      receiving the signal from the sensor;
      transforming the signal based at least in part on a continuous wavelet transform;
      generating the scalogram based at least in part on the transformed signal;
      estimating the one or more energy values in the wedge region of the scalogram based at least in part on an estimation scheme;
      determining one or more signal parameters of the signal based at least in part on the one or more estimated energy values; and
      outputting the determined one or more signal parameters to an output device.

12. The system of claim 11, wherein estimating the one or more energy values comprises:
   determining a plurality of estimation points and a set of locations corresponding to the plurality of estimation points in the wedge region of the scalogram;
   determining a set of estimation parameters corresponding to the estimation scheme; and
   determining a size and shape of a vicinity region.

13. The system of claim 12, wherein the determined size and shape of the vicinity region is based, at least in part, on one or more characteristics of the one or more signal parameters.

14. The system of claim 12, wherein the determined size and shape of the vicinity region is based, at least in part, on one or more characteristics of a patient.

15. The system of claim 11, wherein the signal comprises a photoplethysmograph (PPG) signal received from a sensor.

16. The system of claim 11, wherein the one or more signal parameters comprises a patient oxygen saturation level.

17. The system of claim 11, wherein the one or more signal parameters comprises a patient respiration rate.

18. The system of claim 11, wherein the one or more processors are further capable of:
   determining one or more confidence metrics based at least in part on the one or more estimated energy values; and
   determining if the one or more confidence metrics satisfy a constraint set.

19. The system of claim 18, wherein determining the one or more confidence metrics comprises:
   determining energy values and energy structure in a pulse band of the scalogram; and
   determining energy values and energy structure in a noise band of the scalogram.

20. The system of claim 11, wherein the estimate of at least one energy value in the one or more estimated energy values is based, at least in part, on a set of resolved energy values in a resolved region of the scalogram and a set of estimated energy values in the wedge region of the scalogram.

* * * * *